US012623007B2

(12) United States Patent
Zucker et al.

(10) Patent No.: US 12,623,007 B2
(45) Date of Patent: May 12, 2026

(54) SURFACE SEALING FOR IMPLANTS

(71) Applicant: Qvanteq AG, Zürich (CH)

(72) Inventors: Arik Zucker, Zürich (CH); Armin W. Mäder, Richterswil (CH); Stefano Buzzi, Birmensdorf (CH)

(73) Assignee: Qvanteq AG, Zurich (CH)

( * ) Notice: Subject to any disclaimer, the term of this patent is extended or adjusted under 35 U.S.C. 154(b) by 884 days.

(21) Appl. No.: 16/488,792

(22) PCT Filed: Feb. 23, 2018

(86) PCT No.: PCT/EP2018/054564

§ 371 (c)(1),
(2) Date: Aug. 26, 2019

(87) PCT Pub. No.: WO2018/154069

PCT Pub. Date: Aug. 30, 2018

(65) Prior Publication Data

US 2020/0023100 A1      Jan. 23, 2020

(30) Foreign Application Priority Data

Feb. 24, 2017    (EP) .................................... 17157918

(51) Int. Cl.
*A61L 31/08* (2006.01)
*A61L 31/14* (2006.01)

(52) U.S. Cl.
CPC .............. *A61L 31/08* (2013.01); *A61L 31/088* (2013.01); *A61L 31/148* (2013.01); *A61L 2420/02* (2013.01)

(58) Field of Classification Search
CPC .......... A61L 31/08; A61L 27/34; A61L 31/14; A61L 15/42; B82Y 30/00; A61K 31/66
See application file for complete search history.

(56) References Cited

U.S. PATENT DOCUMENTS 4,906,237 A     3/1990   Johansson et al.
5,441,739 A     8/1995   Kossovsky et al.
(Continued)

FOREIGN PATENT DOCUMENTS

EP          021771    *  8/1990    ............. A61L 31/08
JP        S62-82968 A     4/1987
(Continued)

OTHER PUBLICATIONS

English-language translation of Notice of Reasons for Rejection issued in Japanese Patent Application No. JP 2019-546153 on Aug. 9, 2022.

(Continued)

*Primary Examiner* — Dah-Wei D. Yuan
*Assistant Examiner* — Andrew J Bowman
(74) *Attorney, Agent, or Firm* — Hoffmann & Baron, LLP

(57) ABSTRACT

The present invention relates to an implant for insertion in a body lumen, wherein at least a portion of the surface is arranged to contact a wall of the body lumen and/or bodily fluid flowing through the lumen when the implant is inserted in the body lumen. The abovementioned portion of surface is covered with a surface sealing which is designed to dissolve within about 30 seconds when inserting the implant in the body lumen, such that this portion of surface is exposed to the body lumen. The present invention also relates to a method of manufacturing an implant as above described, comprising the steps of obtaining an implant with a surface; providing at least a portion of such surface with target characteristics; and covering such at least a portion of surface with a surface sealing to preserve the target characteristics. The present invention also refers to an implant set comprising an implant as defined and to a use of such an implant for treating an animal or a human body, wherein the treatment procedure comprises dissolving the surface seal- (Continued)

ing covering at least a portion of a surface of the implant by flushing the surface with a dissolving solution.

22 Claims, 3 Drawing Sheets

(56) References Cited

U.S. PATENT DOCUMENTS

| | | | | |
|---|---|---|---|---|
| 5,830,217 | A | 11/1998 | Ryan | |
| 8,541,498 | B2 * | 9/2013 | Sandhu | A61L 27/34 |
| | | | | 526/263 |
| 2003/0064965 | A1 * | 4/2003 | Richter | A61K 31/66 |
| | | | | 514/102 |
| 2007/0036835 | A1 * | 2/2007 | Coppeta | B82Y 30/00 |
| | | | | 604/890.1 |
| 2008/0226694 | A1 * | 9/2008 | Gelbart | A61L 31/14 |
| | | | | 424/426 |
| 2009/0132048 | A1 | 5/2009 | Denzer | |
| 2010/0168854 | A1 | 7/2010 | Luers et al. | |
| 2011/0152995 | A1 | 6/2011 | Mader et al. | |
| 2011/0166672 | A1 | 7/2011 | Tei et al. | |
| 2011/0178590 | A1 | 7/2011 | Zucker | |
| 2011/0183000 | A1 | 7/2011 | Tei et al. | |
| 2011/0274737 | A1 | 11/2011 | Palmaz | |
| 2012/0150284 | A1 * | 6/2012 | Gratz | A61L 31/08 |
| | | | | 623/1.42 |
| 2012/0216905 | A1 * | 8/2012 | Pacetti | A61L 31/16 |
| | | | | 141/1 |

FOREIGN PATENT DOCUMENTS

| | | | | |
|---|---|---|---|---|
| JP | H 08-505788 | A | 6/1996 | |
| JP | 2010-517729 | A | 5/2010 | |
| JP | 2011-526163 | A | 10/2011 | |
| WO | WO 2010/000080 | A1 | 1/2010 | |
| WO | WO 2010/001578 | A1 | 1/2010 | |
| WO | WO 2010/001601 | A1 | 1/2010 | |
| WO | WO-2013093868 | A1 * | 6/2013 | A61L 15/16 |

OTHER PUBLICATIONS

Crowe, Lois M., et al., "Is Trehalose Special for Preserving Dry Biomaterials?", Biophysical Journal, vol. 71, Oct. 1996, pp. 2087-2093.

Patent Cooperation Treaty Written Opinion and International Search Report dated May 24, 2018.

* cited by examiner

SURFACE SEALING FOR IMPLANTS

CROSS-REFERENCE TO RELATED APPLICATIONS

This application is the U.S. National Phase of, and Applicant claims priority from, International Application No. PCT/EP2018/054564, filed on 23 Feb. 2018, and European Patent Application No. 17157918.8, filed on 24 Feb. 2017, both of which are incorporated herein by reference in their entirety.

TECHNICAL FIELD

The present invention relates to an implant for insertion in a body lumen according to the preamble of the independent claims and more particularly to an implant which, when inserted, comprises at least a portion of a surface arranged to contact a wall of a tubular structure corresponding to the body lumen to and/or to contact bodily fluids flowing therethrough. The present invention also relates to a use of such an implant involving flushing a surface thereof; to a set of such an implant together with a package for storage and/or with a device for the insertion of the implant; and to a method of manufacturing such an implant.

Such an implant for insertion in a body lumen can be a vascular prosthesis, as in the case of a stent. Implants according to the present invention are not exclusively limited to an application to tissues of blood vessels, but can take several forms aptly modified to comply with the anatomic structure of cavities and/or body lumina in different body organs, whether on an inside or on an outside wall of such cavities and/or body lumina. Therefore, an implant according to the present invention can also be an intracranial stent or a flow diverter; or an ocular stent; or a coil or a web-like structure for vascular aneurysm; or a heart valve; or a part of a cardiac pacemaker such as an electrode. Preferably, an implant according to the present invention is designed to come into contact with bodily fluids and employed in anatomical areas which allow a dynamic passage of bodily fluids.

BACKGROUND ART

The surface characteristics of implants configured to be inserted on or in soft tissue of the body, such as stents, are paramount to the success of a treatment of a body lumen by application or insertion of the implant. In fact, treatment by such implants entails risks for the patient due to, among other things, inflammatory reactions and/or to deposition of unwanted substances from the bodily fluids and/or uncontrolled cell proliferation and/or to the development of thromboses on the structures of the implants leading, in their turn, to abnormal narrowing or contractions of body passages or openings, generally named stenosis. Implant surfaces are also liable to contamination by deposits of organic (e.g., natural hydrocarbon molecules present in the atmosphere of cleanroom production facilities, as well as on work gloves in cleanrooms, and/or on production equipment in cleanrooms) or non-organic (e.g., residuals deriving from manufacturing processes such as electro-polishing) matter. Implants such as above introduced, and the respective insertion devices, should be as free as possible of any such contamination. Furthermore, their surfaces should carry no dust, no fibers, no chemical impurities or particles in general.

It is consequently a common practice to impart targeted surface characteristics to the implants such as stents, e.g., in order to grant their surface antithrombotic properties preventing the build-up of thrombi. One way to receive antithrombotic properties is to achieve and preserve high hydrophilicity of the implant surfaces as this reduces platelet adhesion and can additionally foster frictionless, accurate implant insertion—consequently limiting potential tissue damage—and promote early tissue healing. Surfaces which ensure biocompatibility of the implants and their ability to favor fast and complete healing of the body tissue at the place of application are highly desirable.

In order to provide implant surfaces with such preassigned target properties, a number of techniques are currently in use, which can comprise—inter alia—surface coating methods and/or providing implant surfaces with specific macro-, micro- or nano-structures or similar. It is also a known practice to adjusting the implant surface charge state in order to selectively regulate protein deposits, trying to allow only those to adhere, which can prove advantageous and excluding undesired ones during healing process after implantation. A further known practice to make an implant surface hydrophilic is the removal of earlier mentioned contaminants from the implant surface, including also the natural organic contaminants (e.g., hydrocarbon deposits) from the atmosphere. This particular practice does not involve a coating or any other substances adhering to the implant surface. Instead, it is considered a highly purified implant surface, which needs to be preserved from recontamination in order to stay highly hydrophilic and therefore, anti-thrombotic. Such a protection of the surface should not interact with or modify the surface in order to maintain the originally created surface properties.

One customary preservation of the desired implant surface properties (such as, e.g., hydrophilicity) is carried out by keeping the implants immersed in an inert storage medium, contained in a sealed packaging that prevents the implant from recontamination. The inert storage medium does not compromise the implant's surface properties and it can be either gaseous or liquid or a combination thereof. In the case of gaseous storage means, the medium can be, e.g., nitrogen or any noble gas. In the case of liquid storage means, it is generally a sterile solution, such as an isotonic saline solution or another inert solution that does not compromise the implant's surface properties. For example, such a system is described in WO 2010/000080 A1.

The provision of inert medium storage, though, inevitably complicates implant production processes, transportation, as well as handling procedures of the implants before and in the course of implantation. In addition, packaging needs to conform to stringent sealing requirements, and in the case of gaseous storage means, detection of leakage is difficult.

Moreover, a gas and/or liquid tight sealed packaging restricts the sterilization possibilities and, e.g., a gas sterilization technique (e.g., ethylene oxide) is not feasible. Instead, radiation sterilization would be appropriate. Radiation sterilization on the other hand can compromise components of the delivery device that are made of, e.g., certain kinds of polymer, which can degrade under such circumstances.

Particularly a liquid preserving solution or bath at least partially leaves open the problem of weight. Especially for large volume implants, such as, e.g., long endovascular stents, heart valves, etc., the mass of the liquid significantly increases the weight of the final product as compared to a comparable and commonly packaged product. Furthermore, such packaging would end up being bulkier. This would result in increased costs, for shipment, storage, etc.

Moreover, a gaseous storage at least partially leaves open the problem of maintaining the desired chemical and physical characteristics, which have previously imparted to the implant surfaces, unaltered. This is especially true in connection with removal of the implants from their packaging and insertion into (or placement onto) a body lumen. In fact, given that such an implant upon its extraction from the packaging is exposed to contaminating air, thus enabling contamination of the implant surface during preparation for implantation.

Additionally, to a certain extent liquids can be prone to acting themselves as carriers of impurities. By way of example, a storage liquid can disadvantageously transfer polymer contaminants from the package container as such or from a gasket or some other component of the packaging employed, to the surface of an implant.

Therefore, there is a need for an implant for insertion in a body lumen, which allows a stable and reliable preservation of its surface characteristics created by a specific treatment and, e.g., guarantees a high level of surface purity. There may also be a concurrent need to overcome the drawbacks of storage in an inert medium (gaseous or liquid and/or a combination thereof) of such kind of implants, in a way that:
- a simplified, less cumbersome design can be employed for the implant packaging and transport;
- handling of the implants when packing them (in the production) and also when extracting them from the packaging (in the clinic) is made safer and less complex;
- the range of sterilization methods is less limited; and/or
- implantation can be carried out without undue urgency linked to an impending risk of losing or corrupting the implant surface characteristics.

SUMMARY

According to the invention this need is settled by an implant for insertion in a body lumen, as it is defined by the features of the independent claims, and also by a use thereof, by a set of such an implant together with a relative package, for storage and/or with a device for the insertion of the implant, as well as by an implant manufacturing method. Preferred embodiments are subject of the dependent claims.

In particular, the invention deals with an implant for insertion in a body lumen. Such implant comprises a surface, at least a portion of which is arranged to contact a wall of the body lumen and/or to contact bodily fluid flowing therethrough, when the implant is in an inserted state. The drawbacks affecting the prior art are overcome by providing the at least a portion of the implant surface with a surface sealing which covers this portion of the implant surface and is soluble when inserting the implant in the body lumen. Advantageously, thanks to the special conception of the present inventive solution, the at least a portion of the surface of the implant covered by the surface sealing is exposed to the body lumen, when the surface sealing dissolves. Thus, it can be guaranteed that the implant is placed in the body lumen with a perfectly pure implant surface which is optimally preserved to best cooperate with a tissue wall and/or with bodily fluid of a body lumen, particularly in a way that can be free from thrombosis and/or stenosis recurrence. In other words, the quality of the implant surface can be maintained, while the implant is stored under dry conditions. Such preservation can be particularly important for hydrophilic stents or similar implants, of which the surfaces are highly purified and/or highly hydrophilic and quickly become re-contaminated.

The term "when inserting the implant in the body lumen" in context of the invention relates to the time frame where all necessary steps involved with introducing the implant into the body are performed. This may at least include preparatory steps to get the implant ready to be ushered into the body, steps of transferring and transporting the implant within the body, and further preparatory steps before final implantation at the target location to fulfil the implant's function. In particular, it may include the step of unpacking the implant, preparing the implant for providing it through an opening in the body, providing it through an opening in the body and forwarding it inside the body to a target location until shortly before placing it at the target location. Thus, in accordance with the invention the surface sealing can be dissolved as early as during unpacking and preparing the implant, e.g., by flushing it before providing it through the opening in the body. It can also be dissolved while providing it through an opening in the body and forwarding it inside the body until the target location is reached; or, in case of a stent, at latest shortly before expanding it in the target location.

The surface sealing can be designed to dissolve upon contact with bodily fluids flowing through the body lumen, without a need for preventive flushing or partial or total removal. For example, it can be dissolved in blood. Alternatively, it can also be devised to be flushable with a solvent (e.g., saline solution) just before insertion of the implant in the body lumen.

By such a surface sealing, target properties which have been previously created or pre-assigned on the implant surface can be optimally preserved, at least up to when the implant is brought into the body lumen. In particular, a comparably high hydrophilicity which reduces thrombogenicity due to lower adhesion of platelets on hydrophilic surfaces can be maintained or preserved.

As mentioned above, such pre-assigned target surface properties preferably comprise antithrombotic properties, to prevent build-up of thrombi; adjusted surface charge properties, in order to selectively regulate protein deposits and/or to prevent contaminant hydrocarbon deposits; and hydrophilicity, to foster frictionless, accurate implant insertion, therefore limiting potential tissue damage and early tissue healing. For example, Phosphorylcholine (PC) coated stents have a PC coating on the surface which allows to lower the stent surface's thrombogenicity. Such or similar coatings or target surfaces can be protected or saved by the surface sealing according to the invention. Furthermore, such pre-assigned target surface properties may comprise pharmaceutical or medical properties. Such properties can be assigned to the surface by providing a medicament or an active pharmaceutical substance to the surface, which may also be covered and conserved by the surface sealing. In particular, the surface sealing according to the invention allows for protecting and saving the surface of medicament containing implant such as a drug eluting stent or the like.

In the context of the present invention, an implant for insertion in a body lumen, or for overall application to a body lumen, is meant to contact a wall of a typically tubular structure of the body lumen and/or to contact bodily fluids, which follow a lumen provided by such tubular structure.

The term "body lumen" as used in connection with the invention relates to an inside space of a tubular structure inside a human or animal body or to a cavity inside the human or animal body. Body lumen in the sense of the present disclosure can take the form, for instance, of a vascular vessel, such as a vein or an artery or a coronary or intracranial vessel or a natural heart valve; or also that of a tract of gastrointestinal organs such as stomach or colon; of a region of urinary collecting ducts or of renal tubes, or of bile duct, or of reproduction organs; of a tract of lung bronchi or of an eye's drainage system; or a cerebral spinal fluid (CSF) drainage.

On the other hand, the implants dealt within the present disclosure are not meant for recesses or cavities formed in harder tissue, such as bone. Whereas implants according to the present invention achieve a good biocompatibility with bodily fluids, such as, e.g., blood, flowing through and/or around them as well as the soft tissue that grows on them, typically they do not absorb or soak up blood in a way that the blood coagulates or attain osseointegration with surrounding bone tissue.

Implants according to the present invention are preferably elastic and flexible, enabling an adjustment to the shape of a body lumen by deformation. Such a deformation can be induced, for instance in the case of a stent used in a balloon angioplasty procedure; or it can happen by using memory shape materials and/or braided filaments, such as in the case of a self-expanding stent. In the case of a stent, the surface sealing might compromise the mechanical characteristics, such as, e.g., its expansion properties. Therefore, in accordance with the present invention the surface sealing preferably has been dissolved prior the target location is reached; or at latest prior the expansion of the implant at the target location. The implants particularly when being embodied as stents or similar devices may be formed by braided, knitted or woven structures, or by laser cutting.

Preferably, but not exclusively, implants according to the present invention comprise a plain, smooth, unroughened surface unlike what is common for implants for bones, for example. Such a plain surface may also lack—or may have been purposely deprived of—any substantial roughness, or at least any roughness at an interior surface of the implant, or waviness of its topology or any substantial texture or a coating of any kind. This may prove especially advantageous for supporting a thorough cleaning or purification of the implants and, conversely, for preventing contamination from the environment such as ambient atmosphere, from storage means or from manipulation. This is the case of bare metal stents, by way of the example, wherein additionally no coating for elution with active substances is envisaged. In this sense, the preferred, optional absence of specific treatments for integrating a complicated roughness or peak and valley topography in the implants according to the present invention may prove beneficial to making the implants less susceptible to contamination and to formation of thrombi.

The term "plain" as associated with possible embodiments of the implants according to the present invention can indicate a substantially smooth surface whose roughness is comprised in a range of up to 10 micrometer or advantageously up to 5 micrometer. Such a plain surface also poses special requirements with respect to the material of the surface sealing, which must be able to adhere to such a plain surface.

The surface sealing which forms a protective layer over the implant according to the present invention preferably is designed to dissolve within a few seconds, i.e., within 30 or preferably within 20 or 10 seconds, essentially as soon as it comes into contact with blood or washing buffer or other liquid solutions that are used for device flushing during preparation. When being inserted into the body lumen or during flushing prior to insertion it is advantageous to quickly dissolve the protective layer such that the perfectly pure implant surface can be exposed directly upon insertion of the implant. Particularly in case of an expandable or reshapeable implant such as a stent, the implant also has to remain flexible during the placement procedure. A sealing that does not dissolve upon first contact with blood or washing buffer could therefore have a negative impact on deliverability, in particular for self-expanding structures where the undissolved sealing can lock the stent in a certain conformation. A fast dissolving surface sealing also reduces the exposure of the patient to foreign substances.

Preferably, the surface sealing is configured to be dissolved when being inserted to a target location in the body lumen. In particular, the surface sealing preferably is configured to be dissolved when arriving at the target location or before being implanted at the target location. Thereby, it can be configured in accordance with a predefined insertion procedure such that it can be assured that the surface sealing is dissolved when finally implanting it. The term "implanting" as used in this connection can relate to securing the implant at or in the body lumen at the target location. For example, in case of a balloon- or self-expandable stent, implanting or implantation can be or involve the expansion of the stent at the target location. Such a surface sealing allows for preserving original mechanical properties of the implant, such as its expansion properties for example, even though its surface is protected by the surface sealing before and eventually while inserting it. This can be important, for example, when stents or other expandable implants are involved, wherein proper expansion of the implant potentially can be affected by the surface sealing. In case of a non-expanding stent, such as, e.g., an ocular stent, implanting or implantation can be or involve the placement of the stent at the target location.

Preferably, the surface sealing dissolves shortly before, during or after insertion in the body lumen, for instance upon contact with the bodily fluid passing though the body lumen. Thus, the function of shielding the defined implant surface characteristics remains effective at least from applying the surface sealing during production throughout packaging, sterilization, storage, transport and unpacking. As soon as the implant is prepared and ready to be inserted into the body lumen, the function of shielding the implant's surface is not necessary anymore and the surface sealing can be dissolved at this time or at least shortly after insertion of the implant in the body lumen. The implant received in, or on, the given body lumen is consequently in its best condition to ensure success of treatment.

The surface sealing can consist of or comprise various materials which, on the one hand, are soluble in the given time and circumstances and, on the other hand, are biocompatible and tight. Thereby, the term "tight" can particularly relate to gas-tight or, more specifically, tight for contaminations such as deposits of organic (e.g., natural hydrocarbon molecules present in the atmosphere of cleanroom production facilities, as well as on work gloves in cleanrooms, and/or on production equipment in cleanrooms) or non-organic (e.g., residuals deriving from manufacturing processes such as electro-polishing) matter, dust, fibers, chemical impurities or particles in general.

For example, the surface sealing can be made of salt such as sodium chloride (NaCl). However, this is a comparably brittle salt that may have the disadvantage of cracking when movements occur and, therefore, it might relatively easily scale from implant surfaces, especially when subject to movements or stress. The surface sealing could also consist or comprise of non-toxic soluble molecules such as carbohydrate and polymers.

In a preferred embodiment, the surface sealing comprises at least, or consists of, a soluble or water-soluble carbohydrate or a soluble polymer such as polyethylene glycol, a soluble ionic compound or a combination thereof, that does not directly interact with the implant surface other than sealing it. In experiments that led to the present invention, sugars have shown a surprisingly advantageous capability to stably preserve target characteristics provided to implant surfaces. Accordingly, it has been discovered that a sugar film provided to cover implant surfaces according to the present invention forms a sealing which shields such surfaces from an interaction with contaminating agents. Sugars are also highly soluble and have exhibited an unexpected aptitude to adhere and remain attached to plain surfaces of implants according to the present invention, without peeling off the implants, even under some applied mechanical stresses and/or after a prolonged time (i.e., aging) after the sealing has been established onto the surface. In fact, sugars have shown a pronounced elasticity and compliance to deformations, which is an advantageous attribute as it aptly supports flexibility and deformability of implants during, e.g., storage and/or vibrations during transportation/shipment, as is the preferred case for the present invention. Following from the above, sugars can be the preferred substances for a surface sealing according to the present invention.

A soluble carbohydrate to be employed for the surface sealing can be a monosaccharide or sugar alcohol, such as Threitol, Erythritol, Glucose, Fructose, Sorbitol, Galactose, Galactitol, Mannose, Mannitol, Xylitol, Myo-inositol or similar, organic acids such as citric acid, or other substances such as vitamin C.

However, also a soluble di- or trisaccharide can be used, such as Trehalose, Maltotriose, Lactose, Lactulose, Palatinose, Sucrose or similar. Trehalose, in particular, has proven to be especially suitable for creating a surface sealing according to the present invention and also proves extremely stable to elevated temperatures.

The surface sealing can also comprise a composition made of monosaccharides and/or disaccharides and/or tri-saccharides and/or polymeric sugars, optionally combined with other compounds such as polymer or a salt.

For selecting an appropriate or optimal material or substance or sealing agent for the surface sealing, plural factors of the given situation or application are to be taken into account. Considering what is required for sealing a surface of a vascular implant, such as a stent or the like, regarding surface characteristics, sealing flexibility, clinical handling, quality assurance, manufacturing, sterilization, transportation, shelf life, etc., a homogenous, glass-like transparent surface sealing which is stable and fast soluble at the same time is typically desired or beneficial.

For fast solubility and including also the above requirements, mono- and disaccharides and sugar-alcohols as mentioned above are well suitable. Moreover, a mix of such mono- and disaccharides with salt or sugar-alcohol with salt can be beneficial. Whereas, as mentioned above, a pure salt sealing may be less suitable; instead, for example, Trehalose in combination with salt has shown beneficial sealing properties.

Larger molecules like tri-saccharides, such as, e.g., Erlose, are typically not as beneficial due to their lower solubility which might make it difficult to be dissolved in the final application. However, in some applications also such slower soluble tri-saccharide surface sealings might be beneficial.

In summary, the ideal surface sealing forms a homogenous, glass-like transparent, gas-tight covering that is conformal to the implant contour and, for flexible implant structures, flexible. It also has good adhesion to the implant surface and/or to the delivery device (onto which the implant is mounted), has a good solubility (not too fast, not too slow such as, e.g., in the time range mentioned above), has a good drying behaviour (after drying not too brittle), is stable during sterilization such as by radiation or high temperature and/or high humidity ethylene oxide, is bio compatible and has an easy regulatory pathway.

In an example, various materials have been tested and analysed with regard to their suitability for being used as a surface sealing. Thereby, cobalt-chrome (CoCr) stents have been provided with different surface sealings, sterilized either with ethylene oxide (EtOx) or by radiation (e.g., e-beam) and aged at a temperature of 55° C. The sealings have been made of saccharides, i.e., two monosaccharides, two disaccharides and monosaccharide alcohol, disaccharides with salts, polyethylene glycol (PEG) with a molar weight of about 6'000 kg/mol, PEG with a molar weight of 10'000 kg/mol, pure salts, ascorbic acid and citric acid. After aging, the stents and the surface sealings have been visually examined. Thereby, saccharides have nice homogeneous, transparent layers, whereas salt and PEG crystalline and flaking layers. Hydrophilicity was comparably well preserved by all sealing materials except for PEG. In the given test arrangement, it has been shown that saccharides, as well as combinations of saccharides with salts, fulfil the requirements for vascular implants best.

The thickness of the surface sealing covering the implant surface can be in a range of up to few hundred micrometers. The sealing can take the form of a film thin enough to advantageously allow movements and flexibility of implant components, for instance relative movement of portions of a mesh of a tubular coronary stent. The thickness can particularly be thinner than the structures it coats.

In the context of the present invention, an implant surface (thus, also the at least a portion of surface arranged to contact a body lumen wall or a fluid flowing therethrough) can be made of a metal or of a metal alloy. Polymer materials or ceramic materials, or a combination of any of those materials, are also possible. Particularly, implants according to the present invention can be made of cobalt chrome alloys, platinum chrome alloys, Nitinol or stainless steel, as well as pyrolytic carbon, silicon carbide or silicon nitride. Conversely, titanium alloys typically used in the orthopaedic field are not especially preferred, except for Nitinol, as they are not especially favourable to the kind of compression and expansion compliance for instance required in stents as they can break during such plastic deformation and also these alloys are typically highly thrombotic.

Whereas it can be sufficient to provide the at least a part of surface of the implant with the surface sealing, preferably the essentially complete surface of the implant is provided with the surface sealing. Like this, the complete surface can be covered and protected.

Implants according to the present invention can be vascular stents or flow diverters, e.g., for treating bifurcation aneurysm; or ocular stents; or coils or web-like structures for the treatment of vascular aneurysm; or artificial or biological heart valves and/or the cage in which these valves are attached to; or a part of a cardiac pacemaker, such as an electrode, or flow disruptors such as coils, webs or web-like coils, neck bridging devices, intra-aneurysmal stents, occluders, adjustable remodelling meshes, aneurism clips, vena cava filters or other filters used during clinical interventions. In the case of cardiac electrodes, the body lumen can be identified as the pericardium. The vascular stents can be intracranial stents, coronary stents, endovascular/peripheral arterial stents, or endovascular/peripheral venous stents, or shunts such as cerebral spinal fluid (CSF) shunt systems.

In a preferred embodiment, the surface sealing is homogeneous. In particular, the surface sealing may be homogeneous by being made of a single composition. Further, it can be homogeneous by being more or less uniformly distributed over the at least a portion of surface. Such homogeneous surface sealing allows for being uniformly and rapidly dissolved and removed prior or during insertion.

Preferably, the surface sealing is seamlessly covering the at least a portion of surface. Like this, the surface can be uniformly covered and contamination can continuously be prevented.

Further, the surface sealing preferably is gas-tight. Such surface sealing allows for efficiently preventing contamination of the surface through the atmosphere.

Another aspect of the invention relates to method of manufacturing an implant for insertion in a body lumen according to the present invention, comprising the steps of:

obtaining an implant with a surface;
    providing at least a portion of such surface, which is arranged to contact a wall of the body lumen and/or a bodily fluid flowing therethrough, with target characteristics; and
    covering such at least a portion of surface with a surface sealing, so as to preserve the target characteristics imparted.

The surface sealing is soluble when inserting the implant in the body lumen. In other words, it can be dissolved and metabolized within the body/secreted from the body or, it can be dissolved by flushing before introduction into the body, or a combination thereof. At the latest, the dissolution process should be completed at the target location before the final implementation or implantation of the implant at the target location. As explained above, this allows, once the sealing is dissolved, the (portion of) implant surface previously covered with the surface sealing and having preserved target characteristics, is now exposed to the body lumen and the implant can execute its medical function without interference by the sealing. The target characteristics preferably comprise hydrophilicity. In particular, the implant surface may have a comparably high hydrophilicity which is essentially an antithrombotic characteristic and which is to be preserved by the surface sealing.

The manufacturing method preferably further comprises the steps of:

providing a solution of a sealing agent;
    immersing the abovementioned portion of implant surface in the solution or spraying it with the solution; and
    drying the sealing agent on such at least a portion of implant surface to form the surface sealing.

The surface sealing is formed ideally uniformly and consistently over the desired (portion of) implant surface, in a way that no region meant to be sealed is left uncovered or is scaled. This can efficiently be achieved by applying the sealing agent in a solution, for example, between 1% to 10% and, preferably, in a solution between 1% to 6%. This methodology, together with hydrophilic properties of the stent, allows sealing of the narrow crevices, for example, at the intersection of two filaments in a braiding. Such application of a soluble surface sealing onto the prepared or (highly) hydrophilic surface may result in a uniform and seamless covering of the at least a portion of the surface because of its hydrophilic properties. This can be beneficial for manufacturing reasons and for assuring respective quality/specifications such as assuring uniform surface coverage, because sealing of a hydrophobic surface might result in uncovered areas because the (watery) sealing solution might be repelled on some areas of the surface.

The term "sealing agent" can relate to a single substance or plural substances which form the sealing on the surface of the implant. In particular, it can be a substance solved in a liquid and forming the surface sealing when being dried.

Further, a step of arranging the implant in, or on, an insertion device or delivery device can be involved in the manufacturing method. An insertion device can be, for instance, a catheter. By way of example, a catheter is employed to deliver the implant which can particularly be a stent to a treatment site in a lumen of a body organ, typically a vessel, and to deploy the implant in such location. The sealing of the surface of the implant may be performed after or before the implant being mounted to the insertion device or during mounting the implant onto the insertion device.

When drying the sealing agent on the at least a portion of implant surface the implant can be arranged in a package such as in the insertion device or a part thereof. Thereby, the sealing agent can bind or merge the implant to the package such that that package and implant form a unit.

Preferably, the manufacturing method comprises flushing the delivery device together with the mounted implant, or while mounting the implant, with a solution of a sealing agent. Like this, the sealing agent can be provided all over the implant and other elements to be inserted into the body or body lumen.

Stents, which are generally cylindrical prostheses, normally enter the body lumen in a configuration with a reduced diameter and are subsequently expanded to the vessel diameter, thus physically supporting vessel walls and keeping the vessel unobstructed. An angioplasty balloon can be used to activate stents which are crimped onto a balloon catheter assembly, in the case of balloon-expandable stents.

Otherwise, self-expanding stents, similar as flow diverter, flow disruptors, coils etc., are spring-loaded into a catheter sheath and their deployment happens by elastic outward expansion into the vessel. In this case, stents profit from shape memory properties of advanced metal materials such as Nitinol (additionally characterized by superelasticity) or special polymer materials (possibly also degradable) or special designs (such as a braided structure) and/or a combination thereof.

Particularly in embodiments where the implant is a stent, the manufacturing method can further comprise a step of crimping the implant before, during or after covering the at least a portion of surface with the surface sealing.

A sealing agent made of sugar can be advantageously stable and elastic to an extent that, e.g., implant crimping is enabled without a risk of scaling off or losing the surface sealing. It has been found that, e.g., Trehalose is especially stable, both when undergoing mechanical and thermal stresses, and suitable to maintain formerly created implant surface characteristics unaltered.

Further, a step of sterilising the implant according to the present invention can follow the formation of the surface sealing, by applying a radiation or a gas. To this purpose, gamma or beta radiations and/or a gaseous sterilisation agent can be used, such as ethylene oxide (ETO) or similar.

Preferably, covering the at least a portion of surface with a surface sealing comprises configuring the surface sealing to be dissolved when being inserted to a target location in the body lumen. Thereby, the surface sealing preferably is configured to be dissolved when being implanted at the target location. Such configuration of the surface sealing can comprise obtaining information about an insertion procedure for the implant intended to be delivered and adapting the surface sealing such that the surface sealing is dissolved when arriving to the target location in accordance with the insertion procedure. The surface sealing is advantageously configured such that it dissolves no later than the final deposition of the implant at the target location. Like this, an implant can be provided with the surface sealing being ready-made for the intended insertion procedure. For example, when the insertion procedure involves a step of flushing the implant upon or shortly before entering the body, the surface sealing can be configured to be dissolved in such flushing. Thus, it can be assured that the surface sealing is removed and the mechanical properties of the implant are available when being at the target location.

A further aspect of the present invention is directed to an implant set comprising an implant as defined above and a package configured to protect the surface of the implant. Advantageously, such package further reinforces protection from shocks or other mechanical/thermal stresses, scratches etc. to the surface sealing, ultimately contributing to the preservation of the target characteristics imparted to the implant surface. This package can also take the form of an insertion device or part thereof, for instance of a catheter, within which the implant is arranged. For example, such package can be or comprise a sheath of the catheter or catheter like arrangement and/or its dispenser coil. The package can be made of a polymer, or another material commonly used for packaging, or a combination thereof. It can comprise a cover for opening and/or closing the package. Furthermore, the cover can be equipped with a pierceable structure such as a septum or the like. Such a structure allows for providing a medium such as a solvent, e.g., a saline solution, into the package, e.g., via a needle such as by means of a syringe or the like without opening it. The package allows for maintaining the integrity of the implant surface.

Advantageously, the package is embodied such that the implant can be flushed by a liquid dissolving the surface sealing. Thereby, the package can be arranged to allow such flushing while the implant is still covered by the package.

As opposed to prior art solutions which rely on liquid substances in the implant container, the package according to the present invention is configured to store the implant in a dry condition, that is, without use of a liquid or gel-like storage means.

The implant set of the present invention can further comprise a pouch, configured to receive the implant and the package for storage. The pouch is preferably permeable to a gaseous sterilising agent and/or radiation sterilisable. Thus, the above-described step of sterilisation can be executed through such especially modified pouch.

When using such a pouch the implant set preferably is, after sterilization, packed in a further bag, envelope, sheath or the like. Like this, it can be achieved that after sterilisation and during long-term storage, inner content of the permeable pouch can be protected from, e.g., moisture.

Moreover, the implant set can comprise the insertion device which is used for inserting an implant according to the present invention in a body lumen, wherein the implant is arranged in or on the insertion device, as above illustrated.

Another further aspect of the present invention refers to a use of an implant as defined above for treating an animal or a human body. More specifically, such use comprises dissolving a surface sealing covering at least a portion of a surface of the implant by flushing the surface with a solvent or dissolving solution. For example, flushing can be performed with water or a water-based saline solution. Flushing can happen once the implant has been taken out of the relative package and is ready for insertion. By implementing an otherwise optional flushing operation, for instance letting a dissolving solution such as water or a sodium chloride solution pass through a catheter to the implant, exposure of the implant surface of the implant to the body lumen can be further promoted or accelerated. Depending on the flushing conditions, dissolution of the surface sealing can also be substantially completed by the time the implant is inserted in the body lumen.

As explained, the solvent or dissolving solution can be deliverable to the implant via an insertion device that is in fluid communication therewith. Thereby, the insertion device preferably is a catheter.

Preferably, the implant set is embodied such that the implant is solubly bound to the package. Such binding can be provided by the manufacturing method as described above. Binding or merging the implant and the package allows for efficiently protecting the implant surface, e.g., by preventing friction between package and implant surface. When or shortly before inserting the implant, it preferably is flushed inside or via the package such that the surface sealing is dissolved and the implant is released from the package.

BRIEF DESCRIPTION OF THE DRAWINGS

The implant according to the invention, as well as a relative implant set and its use, are described in more detail herein below by way of an exemplary embodiment and with reference to the attached drawings, in which:

FIG. 1e schematically shows how the dissolving of the soluble surface sealing of FIG. 1d when the implant is inserted in a body lumen exposes an implant surface which is substantially the same as the surface resulting from preparation and treatment in FIG. 1a;

DETAILED DESCRIPTION

Figure 1A:
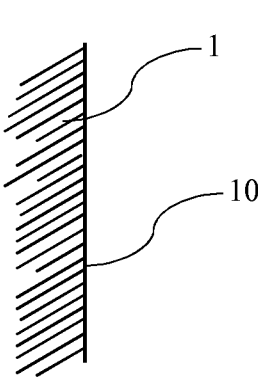
FIG. 1a schematically shows a portion of an implant surface as ideally resulting from surface preparation and treatment aimed at imparting target surface characteristics which make the implant best suited for an intended treatment.

In the following description, certain terms are used for reasons of convenience and are not intended to limit the invention. The terms "right", "left", "up", "down", "under" and "above" refer to directions in the figures. The terminology comprises the explicitly mentioned terms as well as their derivations and terms with a similar meaning. Also, spatially relative terms, such as "beneath", "below", "lower", "above", "upper", "proximal", "distal", and the like, may be used to describe one element's or feature's relationship to another element or feature as illustrated in the figures. These spatially relative terms are intended to encompass different positions and orientations of the devices in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. The devices may be otherwise oriented (rotated 90 degrees or at other orientations), and the spatially relative descriptors used herein interpreted accordingly. Likewise, descriptions of movement along and around various axes include various special device positions and orientations.

To avoid repetition in the figures and the descriptions of the various aspects and illustrative embodiments, it should be understood that many features are common to many aspects and embodiments. Omission of an aspect from a description or figure does not imply that the aspect is missing from embodiments that incorporate that aspect. Instead, the aspect may have been omitted for clarity and to avoid prolix description. In this context, the following applies to the rest of this description: If, in order to clarify the drawings, a figure contains reference signs which are not explained in the directly associated part of the description, then it is referred to previous or following description sections. Further, for reason of lucidity, if in a drawing not all features of a part are provided with reference signs it is referred to other drawings showing the same part. Like numbers in two or more figures represent the same or similar elements.

As explained above, given the relevant influence of implant surfaces on critical aspects of healing, such as thrombotic, inflammatory, and hyperplastic responses, it has been found that preventively assigning certain target surface characteristics to the implants, before insertion, is advantageous. In fact, contamination of implant surfaces with industrial impurities; unsuitable physical and chemical properties of these implant surfaces or a wrong distribution of electrostatic forces on them can account for unfavourable protein interaction (e.g., proteins of blood and tissue of the body lumen wall), uneven cellular attachment and unpredictable healing patterns, ultimately affecting the procedural outcome.

In particular, implant surfaces can be designed to incorporate antithrombotic properties preventing the build-up of thrombi; and/or hydrophilicity and/or a given surface charge. An exemplary surface 10 of an implant 1 is shown in FIG. 1a, as resulting from treatment which effectively assigned such targeted characteristics.

Figure 1B:
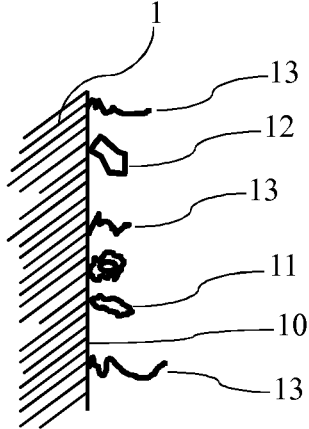
FIG. 1b schematically shows the onset of contamination on an implant surface which has not been adequately shielded from the environment and exemplifies how the ideal implant surface can be quickly lost by alteration of the originally desired properties.

However, if such targeted characteristics are not appropriately preserved, the implant surface 10 can be quickly, adversely affected and the preventively engineered surface characteristics are compromised by environment contaminants, such as hydrocarbon deposits or deposits of other undesired organic matter 11, machining impurities 12, fibers, dust etc. For example, this can result in a loss of surface hydrophilicity. In addition to that, the implant surface might not be able to selectively regulate protein deposits, thus failing to hinder adhesion of undesired proteins and/or proteins in undesired state, such as, e.g., denatured 13. This is exemplified in FIG. 1b.

Figure 1C:
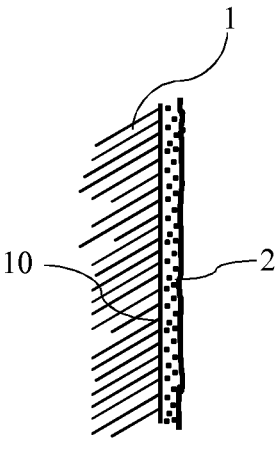
FIG. 1c schematically shows a portion of a surface of an implant according to the present invention, wherein a soluble surface sealing has been promptly applied to preserve the target characteristics preventively imparted to the implant surface.
Figure 1D:
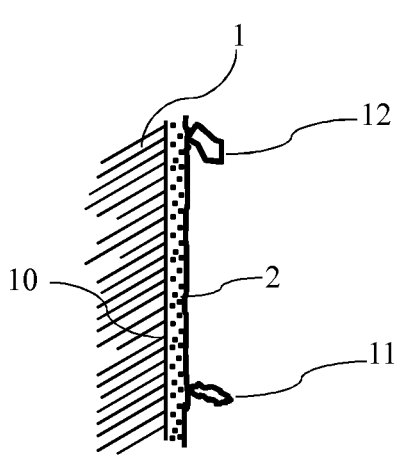
FIG. 1d schematically shows the portion of the surface of the implant, wherein the soluble surface sealing is applied and contaminated.
Figure 1E:
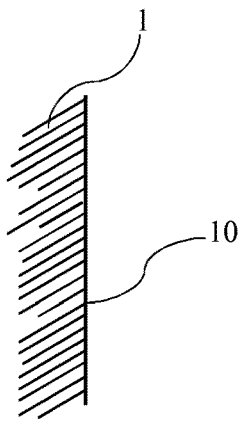

In FIG. 1c is represented a portion of a surface 10 of an implant which is arranged to contact a wall of a body lumen and/or bodily fluids flowing therethrough. The surface 10 is covered with a protective surface sealing 2 according to the present invention. As can be seen in FIG. 1d, the surface sealing can also be contaminated. However, potential contaminations are limited to the surface of the sealing and cannot reach the protected surface. The solubility of the sealing 2 when implanting the implant 1 in the body lumen is engineered so that the surface 10 is exposed to the body lumen and all the necessary interactions between bodily fluid and/or wall of the body lumen, on the one hand, and implant surface 10, on the other hand, effectively happen as intended, e.g., consistently with the preserved target characteristics provided to the surface 10. The perfectly preserved surface 10 is exemplified in Fig. 1e after the sealing being dissolved and, thus, the contaminations being removed with the surface sealing. As already illustrated above more in detail, the surface sealing 2 preferably comprises at least, or consists of, a soluble carbohydrate. Trehalose has proved particularly suitable to create the surface sealing 2.

The covering by the sealing 2 can be implemented by providing a solution of a sealing agent, i.e., a solution of the mentioned carbohydrate. The application to the implant 1 can happen by immersion of the chosen at least a portion of the surface 10 in the sealing agent solution. Drying can follow so that the surface sealing 2 is formed.

Figure 2:
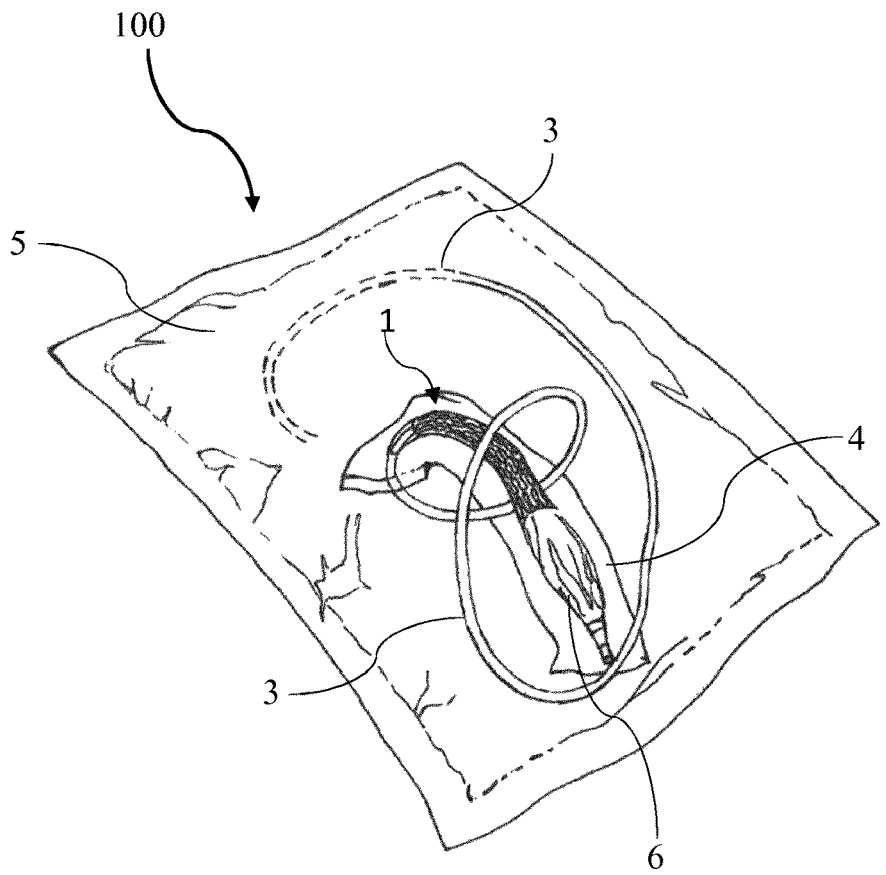
FIG. 2 shows a possible embodiment of an implant set according to the present invention, in the specific case of a balloon-inflatable stent.

In FIG. 2, an implant set 100 according to the present invention is represented. Relative to the embodiment illustrated, the implant is a balloon-expandable stent 1 which is crimped onto a balloon 6 assembled on a catheter 3 for inserting and delivering the stent 1 to the desired location in a body lumen.

The implant set 100 comprises also a package 4 configured to protect the surface 10 of the stent 1. The package 4 is especially conceived to prevent damage to the surface 10 of the stent 1 from shocks, other mechanical or thermal stresses, from scratches and similar, and/or from moisture. Thanks to the provision of the sealing 2 according to the present invention, and differently from the prior art systems, no need for a liquid or gel-like storage means is needed and the package 4 is configured to store the stent 1 in a dry condition. This configuration can be more practical, safe, space-saving and economic than that required for a wet storage.

A pouch 5 can be provided in the implant set 100, which is configured to receive the stent 1, the relative package 4 and, in this case, also the catheter 3. In the embodiment of FIG. 2, the assembly of stent 1, catheter 3 and package 4 is fully contained in the pouch 5.

The stent 1, as well as the other components of the set 100, can be sterilised by applying a radiation or a gas, subsequently to the step of covering the at least a portion of surface 10 with the surface sealing 2. Relative to the embodiment of FIG. 2, sterilisation can be achieved through pouch 5. In fact, pouch 5, as well as package 4, can be made permeable to a gaseous sterilising agent, such as ethylene oxide (ETO) or similar, and/or radiation sterilisable, for instance by gamma or beta radiation.

The stent 1 is usable for treatment of an animal or a human body. The treatment procedure can encompass flushing the surface 10 with a dissolving solution to dissolve the surface sealing 2. In the configuration of FIG. 2, the dissolving would preferably take place once the stent 1 has been taken out of the pouch and of the package 4 and is ready for insertion. Such flushing can enhance the solubility of the sealing 2 and reduce the time interval after which the inserted stent surface 10 is exposed to a body lumen or completely remove the sealing immediately prior to implantation. The dissolving solution can be delivered to the stent surface 10 via the catheter 3 which is in fluid communication with the stent 1. Alternatively, in case the package 4 is embodied with an opening that is covered by a cover, the cover can be equipped with a septum or a similar structure which can be pierced for providing a solvent to the stent 1.

Figures 3, 4:
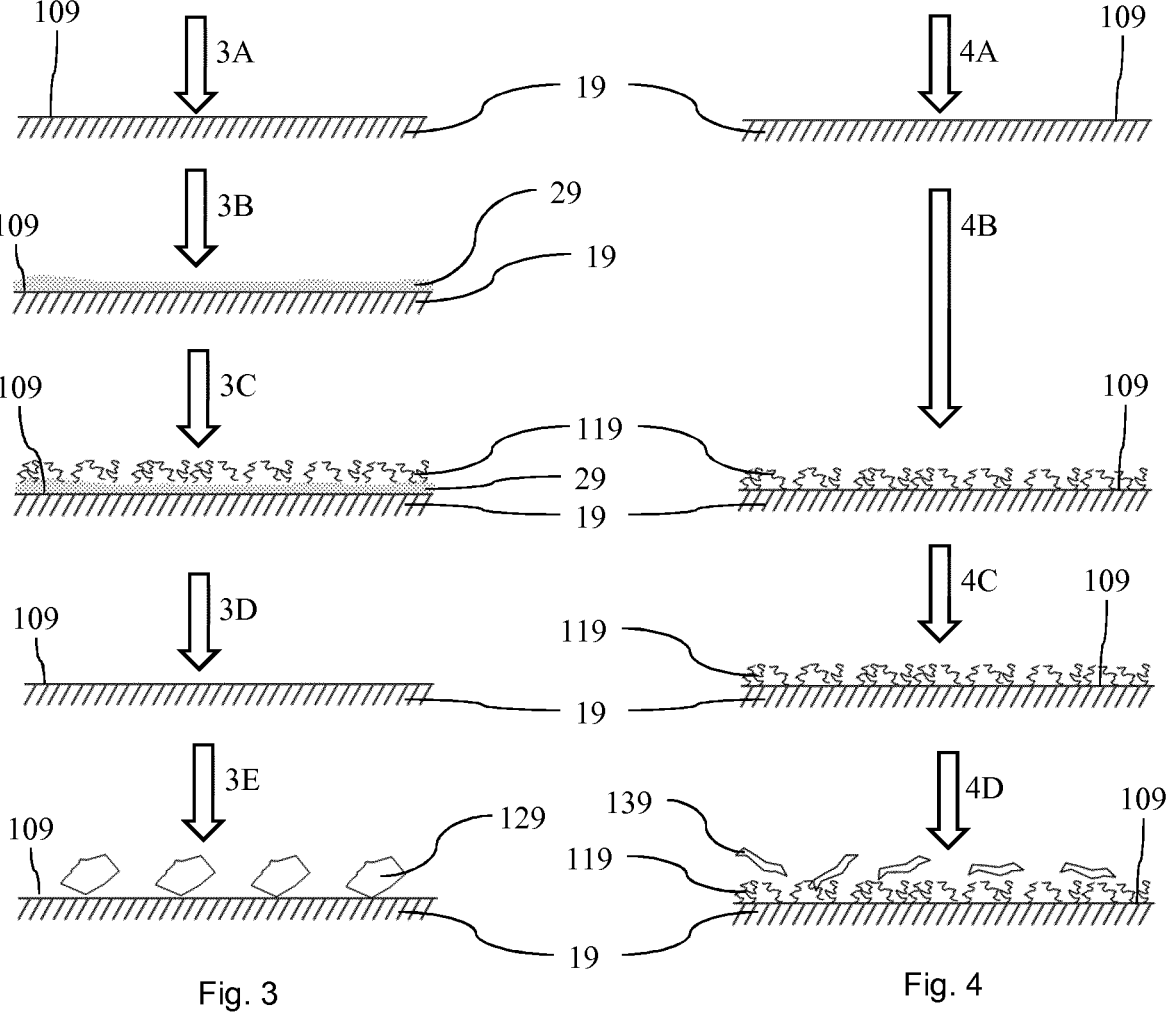
FIG. 3 shows an embodiment of a use according to the invention.
FIG. 4 shows a conventional use of a stent.

In FIG. 3 a use of a stent 19 for implantation into a human body is shown. In a first step 3A a surface 109 of the stent 19 is hydrophilized and purified such that stent surface 109 is obtained in a highly purified state having target characteristics advantageous for implantation into a blood vessel as body lumen.

Then, in a second step 3B as an embodiment of a manufacturing method according to the invention, a solution of a sealing agent is provided, the stent 19 is immersed in this solution and the sealing agent is dried on the at least a portion of surface such that a layer of Trehalose is formed as surface sealing 29 on the surface 109 of the stent 19. Like this, surface 109 is covered with the surface sealing 29 to preserve the target characteristics and an embodiment of implant according to the invention results.

In step 3C, the stent 19 is stored. Over time, natural and eventually other contaminations 119 are collected and adhered on the surface sealing 29 of the stent 19. Such natural contaminations 119 can comprise, e.g., hydrocarbons from the atmosphere.

Later, the stent 19 is implanted into the blood vessel, e.g., by means of a catheter. When inserting the stent 19 into the body, in step 3D, it is flushed with a saline solution. Thereby, the surface sealing 29 is dissolved and washed away together with the contaminations 119. After flushing, the stent surface 109 is again in the highly purified state having the target characteristics. Like this, the stent 19 is inserted into the body lumen at its target position.

In step 3E, the stent 19 is in the blood vessel at its target position. Since the stent surface 109 is essentially free of any contaminations 119, desired proteins 129 are accumulating on the stent surface 109 of the implanted stent 19.

In comparison to the use of FIG. 3, FIG. 4 shows a conventional use of a stent 19 for implantation into a human body. There, in a first step 4A a surface 109 of the stent 19 is hydrophilized and purified such that stent surface 109 is obtained in a highly purified state having target characteristics advantageous for implantation into a blood vessel as body lumen.

In step 4B, the stent 19 is stored. Over time, natural and eventually other contaminations 119 are collected and adhered on the surface 109 of the stent 19.

Later, the stent 19 is implanted into the blood vessel. When inserting the stent 19 into the body, in step 4C, it is flushed with a saline solution. After flushing, the stent surface 109 is still at least to a certain extent covered by the contaminations 119. In this state, the stent 19 is inserted into the blood vessel at its target position.

In step 4D, the stent 19 is in the blood vessel at its target position. Since the stent surface 109 contains contaminations 119, undesired proteins 139 such as denatured proteins are accumulated on the stent surface 109 of the implanted stent 19.

This description and the accompanying drawings that illustrate aspects and embodiments of the present invention should not be taken as limiting the claims defining the protected invention. In other words, while the invention has been illustrated and described in detail in the drawings and foregoing description, such illustration and description are to be considered illustrative or exemplary and not restrictive. Various mechanical, compositional, structural, electrical, and operational changes may be made without departing from the spirit and scope of this description and the claims. In some instances, well-known circuits, structures and techniques have not been shown in detail in order not to obscure the invention. Thus, it will be understood that changes and modifications may be made by those of ordinary skill within the scope and spirit of the following claims. In particular, the present invention covers further embodiments with any combination of features from different embodiments described above and below.

The disclosure also covers all further features shown in the Figs. individually although they may not have been described in the afore or following description. Also, single alternatives of the embodiments described in the figures and the description and single alternatives of features thereof can be disclaimed from the subject matter of the invention or from disclosed subject matter. The disclosure comprises subject matter consisting of the features defined in the claims or the exemplary embodiments as well as subject matter comprising these features.

Furthermore, in the claims the word "comprising" does not exclude other elements or steps, and the indefinite article "a" or "an" does not exclude a plurality. A single unit or step may fulfil the functions of several features recited in the claims. The mere fact that certain measures are recited in mutually different dependent claims does not indicate that a combination of these measures cannot be used to advantage. The terms "essentially", "about", "approximately" and the like in connection with an attribute or a value particularly also define exactly the attribute or exactly the value, respectively. The term "about" in the context of a given numerate value or range refers to a value or range that is, e.g., within 20%, within 10%, within 5%, or within 2% of the given value or range. Components described as coupled or connected may be electrically or mechanically directly coupled, or they may be indirectly coupled via one or more intermediate components. Any reference signs in the claims should not be construed as limiting the scope.

The invention claimed is:

1. An implant for insertion in a body lumen, the implant comprising:

a surface, at least a portion of the surface being arranged to contact a wall of the body lumen and/or bodily fluid flowing therethrough when the implant is inserted in the body lumen at a target location, wherein the at least a portion of the surface is a plain surface provided with assigned target characteristics comprising at least hydrophilicity, wherein the at least a portion of the surface and thus the plain surface is made of a metal or of a metal alloy, or of a ceramic material, or of a combination thereof, wherein the at least a portion of the surface is covered with a gas-tight surface sealing which adheres directly to the plain surface and is configured to dissolve during insertion of the implant in the body lumen, such that the surface sealing has been dissolved and at least a hydrophilic portion of the plain surface is exposed to the body lumen prior to the target location being reached, wherein the surface sealing consists of a soluble carbohydrate being a monosaccharide or a sugar alcohol, or being a disaccharide, or a combination thereof, and wherein a thickness of the surface sealing is in a range of up to a few hundred micrometers and is thinner than a structure of the implant it coats, the surface sealing configured to provide elasticity that supports flexibility and deformability of the implant capable of preserving the assigned target characteristics of the at least a portion of the surface.

2. The implant of claim 1, wherein the monosaccharide or the sugar alcohol is one or more of Threitol, Erythritol, Glucose, Fructose, Sorbitol, Galactose, Galactitol, Mannose, Mannitol, Xylitol, or Myo-inositol.

3. The implant of claim 1, wherein the implant is a vascular stent;

or a flow diverter; or an ocular stent; or a coil or web-like structure for the treatment of vascular aneurysm; or a heart valve; or a cage of a heart valve; or a part of a cardiac pacemaker such as an electrode; or a shunt.

4. The implant of claim 1, wherein the target characteristics further comprise an antithrombotic property and/or a surface charge.

5. The implant of claim 1, wherein the surface sealing is homogeneous.

6. The implant of claim 1, wherein the plain surface lacks a roughness or waviness of its topology, or a texture, or a combination thereof.

7. The implant of claim 1, wherein the surface sealing seamlessly covers the at least a portion of the surface.

8. The implant of claim 1, wherein the metal or the metal alloy is one of a cobalt chrome alloy, a platinum chrome alloy, Nitinol or stainless steel.

9. The implant of claim 1, wherein the wherein the plain surface lacks a coating.

10. The implant of claim 1, wherein the disaccharide is one or more of Trehalose, Lactose, Lactulose, Palatinose, or Sucrose.

11. The implant of claim 1, wherein the surface sealing is dissolvable within 30 seconds.

12. An implant for insertion in a body lumen, the implant comprising:

a surface, at least a portion of the surface being arranged to contact a wall of the body lumen and/or bodily fluid flowing therethrough when the implant is inserted in the body lumen at a target location, wherein the at least a portion of the surface is a plain surface provided with assigned target characteristics comprising at least hydrophilicity, wherein the at least a portion of the surface and thus the plain surface is made of a metal or of a metal alloy, or of a ceramic material, or of a combination thereof, wherein the at least a portion of the surface is covered with a gas-tight surface sealing which adheres directly to the plain surface and is configured to dissolve no later than the final deposition of the implant at the target location, such that the-at least a hydrophilic portion of the plain surface is exposed to the body lumen, wherein the surface sealing consists of a soluble carbohydrate being a monosaccharide or a sugar alcohol, or being a disaccharide, or a combination thereof, and wherein a thickness of the surface sealing is in a range of up to a few hundred micrometers and is thinner than a structure of the implant it coats, the surface sealing configured to provide elasticity that supports flexibility and deformability of the implant capable of preserving the assigned target characteristics of the at least a portion of the surface.

13. The implant of claim 12, wherein the monosaccharide or the sugar alcohol is one or more of Threitol, Erythritol, Glucose, Fructose, Sorbitol, Galactose, Galactitol, Mannose, Mannitol, Xylitol, or Myo-inositol.

14. The implant of claim 12, wherein the implant is a vascular stent;

or a flow diverter; or an ocular stent; or a coil or web-like structure for the treatment of vascular aneurysm; or a heart valve; or a cage of a heart valve; or a part of a cardiac pacemaker such as an electrode; or a shunt.

15. The implant of claim 12, wherein the target characteristics further comprise antithrombotic property and/or a surface charge.

16. The implant of claim 12, wherein the surface sealing is homogeneous.

17. The implant of claim 12, wherein the plain surface lacks a roughness or waviness of its topology, or a texture, or a combination thereof.

18. The implant of claim 12, wherein the surface sealing seamlessly covers the at least a portion of the surface.

19. The implant of claim 12, wherein the metal or the metal alloy is one of a cobalt chrome alloy, a platinum chrome alloy, Nitinol or stainless steel.

20. The implant of claim 12, wherein the plain surface lacks a coating.

21. The implant of claim 12, wherein the disaccharide is one or more of Trehalose, Lactose, Lactulose, Palatinose, or Sucrose.

22. The implant of claim 12, wherein the surface sealing is dissolvable within 30 seconds.

* * * * *